United States Patent [19]

Brady et al.

[11] Patent Number: 5,585,542
[45] Date of Patent: Dec. 17, 1996

[54] DNA SEQUENCES ENCODING AT LEAST PART OF THE TOMATO ENZYME ENDOPOLYGALACTURONASE PG1 β-SUBUNIT

[75] Inventors: Colin Brady; Elizabeth Lee; Barry J. Pogson; Glenda R. Orr; James Speirs, all of Sydney, Australia

[73] Assignee: Commonwealth Scientific and Industrial Research Organisation, Campbell, Australia

[21] Appl. No.: 81,259

[22] PCT Filed: Dec. 20, 1991

[86] PCT No.: PCT/AU91/00594

§ 371 Date: Oct. 25, 1993

§ 102(e) Date: Oct. 25, 1993

[87] PCT Pub. No.: WO92/11374

PCT Pub. Date: Jul. 9, 1992

[30] Foreign Application Priority Data

Dec. 21, 1990 [AU] Australia ................... PK4037

[51] Int. Cl.⁶ ................ A01H 4/00; C07K 14/415; C12N 15/29; C12N 15/82
[52] U.S. Cl. ................ 800/205; 800/DIG. 44; 536/23.2; 435/320.1; 530/370; 530/379
[58] Field of Search ............ 536/23.2; 435/320.1, 435/172.3, 69.1; 530/370, 379, 416; 800/205, DIG. 44

[56] References Cited

PUBLICATIONS

Compton, T. "Degenerate Primers for DNA Amplification" PCR Protocols: A Guide to Methods and Applications, Academic Press, pp. 39–45. 1990.
Lee, C. C. et al. "cDNA cloning using . . . " PCR Protocols: A Guide to Methods and Applications, 1990, Academic Press, pp. 47–53.
Frohman, M. A., et al. "Rapid production of full–length . . . " Proc. Natl Acad. Sci., vol. 85, Dec. 1988, pp. 8998–9002.
Frohman, M. A. "Race: Rapid amplification . . . " PCR Protocols: A Guide to Methods and Applications, Academic Press, pp. 27–38. 1990.
Smith, C. J. S. et al. "Antisense RNA inhibition . . . " Nature, vol. 334, 25 Aug. 1988, pp. 724–726.
Fillatti et al. "Efficient transfer of a gluphosate . . . " Biotechnology, vol. 5, Jul. 1987, pp. 726–730.
Hamilton et al. Nature, vol. 346, 19 Jul. 1990, pp. 284–286.
Shahin, E. A. et al. "Transformation of cultivated . . . " Theor Appl Genet (1986), 72, pp. 720–777.
Sheehy, R. E. et al. "Reduction of polygalacturonase . . . " Proc. Natl Acad. Sci. USA, vol. 85 (Dec. 1988), pp. 8805–8809.
Pogson, B. J. et al. "On the occurrence and structure of subunits . . . " Aust. J. Plant Physiol. 1991, 18, pp. 65–79.
J. E. Lincoln et al. "Diverse mechanisms for the regulation . . . " Mol. Gen.–Genet (1988) 212, pp. 71–75.
Moshrefi, M. et al "Carbohydrate composition and electrophoretic . . . " European Journal of Biochemistry, vol. 135 No. 3, Oct. 1983, pp. 511–514.
Osteryoung, K. W. et al. "Analysis of tomato polygalaturonase . . . " The Plant Cell, vol. 2 No. 12, Dec. 1990, Rockville, MD, USA, pp. 1239–1248.
Pressey, R. "Purification and characterization of tomato . . . " European Journal of Biochemistry, vol. 144 No. 2, Oct. 1984, pp. 217–221.
Smith, et al (Aug. 1988) Nature 334: 724–726.
Zheng, et al (Sep. 1992) The Plant Cell 4: 1147–1156.
Moshrefi, et al (1983) European Journal of Biochemistry 135 (3): 511–514.
Pressey (Oct. 1984) European Journal of Biochemistry 144(2): 217–221.

*Primary Examiner*—Che S. Chereskin
*Attorney, Agent, or Firm*—Nixon & Vanderhye

[57] ABSTRACT

The present invention provides an isolated DNA sequence which encodes at least part of the tomato enzyme endopolygalacturonase PG1 beta-subunit. This DNA sequence preferably encodes a polypeptide, the N-terminal amino acid sequence of which is: E-K-H-S-G-D-I-H. In other preferred forms of the invention the DNA sequence encodes a polypeptide which includes one of the following amino acid sequences: E-K-H-S-G or N-Y-G-Q-X-F-N-E-G. The DNA sequence of the present invention may be used to produce genetically engineered tomato plants with modified ripening characteristics.

13 Claims, 6 Drawing Sheets

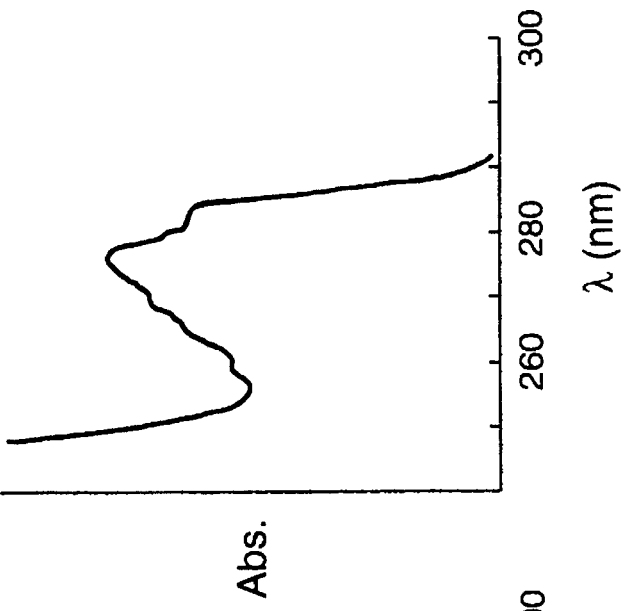
FIG. 2A PG2
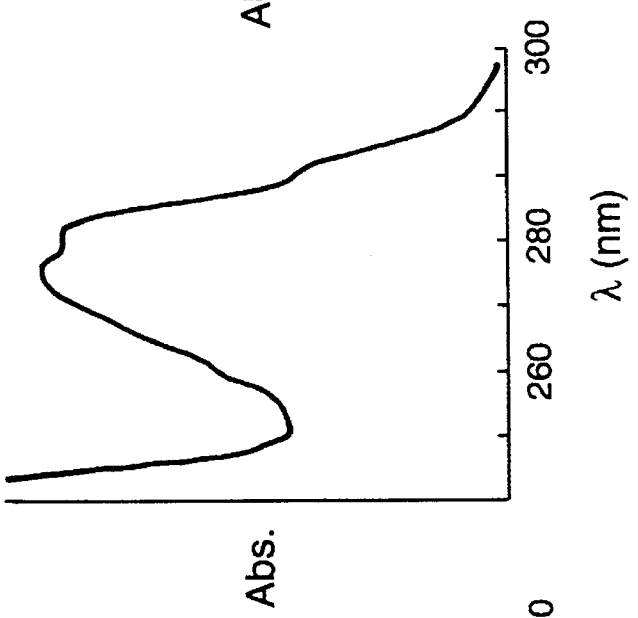
FIG. 2B PG1
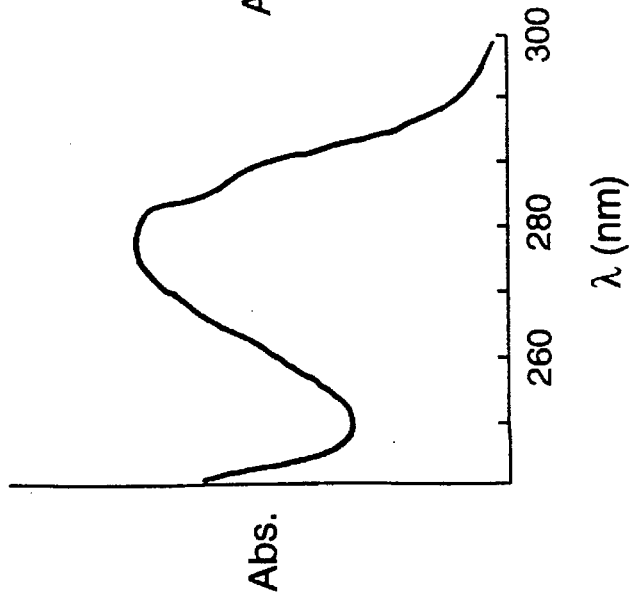
FIG. 2C B-SUBUNIT

PG1

PG1

PG2

PG2

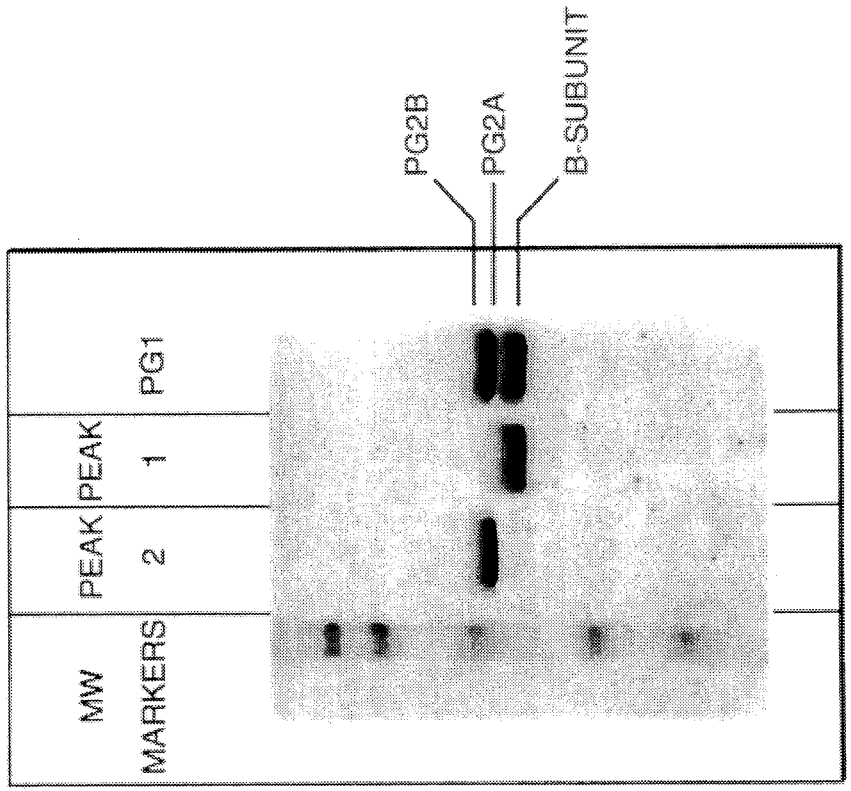
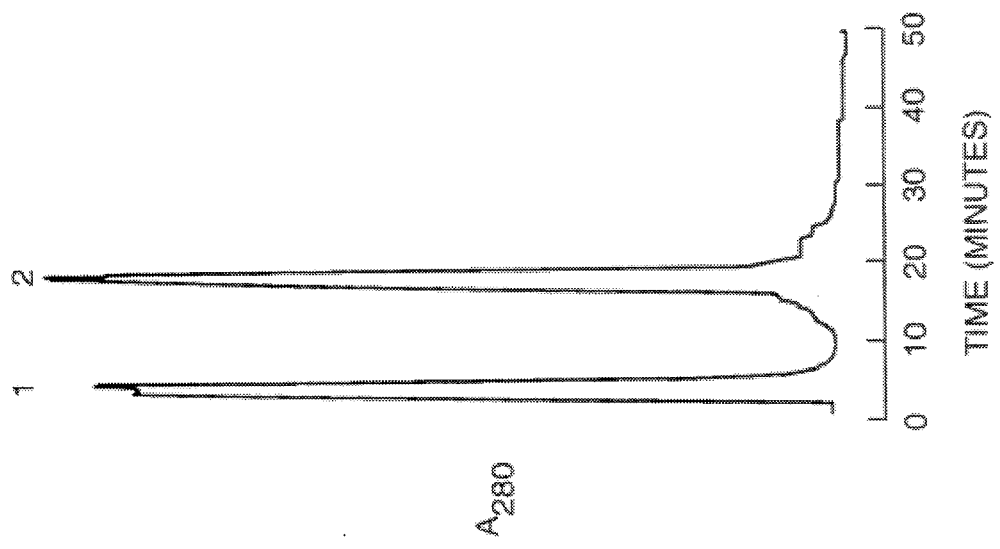

DNA SEQUENCES ENCODING AT LEAST PART OF THE TOMATO ENZYME ENDOPOLYGALACTURONASE PG1 β-SUBUNIT

FIELD OF THE INVENTION

The present invention relates to a DNA sequence which encodes at least part of the tomato enzyme endopolygalacturonase PG1 β-subunit. The present invention further relates to the use of this DNA sequence in modulating endopolygalacturonase expression in tomatoes.

BACKGROUND OF THE INVENTION

The structure of tomato fruit endopolygalacturonase (EC 3.2.1.15, poly (1,4 α-D-galacturonide) glycanohydrolase or PG) resides in three proteins termed PG1, PG2A and PG2B (Ali and Brady 1982). The three proteins are immunologically related (Ali and Brady 1982) and appear to be, in part, the products of a single copy gene that is developmentally regulated (Bird et al. 1988). PG1 apparently also contains another polypeptide (Moshrefi and Luh 1983). The gene, DNA copies of the mRNA encoding PG2A, and the PG2A form of the protein have been sequenced (Bird et al. 1988; Grierson et al. 1986; Sheehy et al. 1987).

As ripening is induced in tomato fruit the following increase: transcription of the PG gene (DellaPenna et al. 1989), the steady state level of the PG mRNA (DellaPenna et al. 1986; Maunders et al. 1987), PG activity and the amount of PG protein (Brady et al. 1982; Tucker and Grierson 1982). Concomitantly, during ripening there is an increase in the ease of pectin extraction and in the compressibility ('softness') of the fruit pericarp (Sawamura et al. 1978; Brady et al. 1982; Seymour et al. 1987). These correlations led to the hypothesis that PG activity is primarily responsible for the increase in softness during ripening (Grierson 1985).

Several aspects of the function and regulation of PG activity in tomato fruit remain unclear. The occurrence and roles of the three isoforms of the enzyme are undefined; the details of their movement to, and interaction with, the cell wall are unknown.

It may be significant that PG1 is the predominant isoform when the total amount of enzyme is small. This is the case in the slow ripening (Nr) mutant, in hetarozygotes of the non-ripening (nor) and ripenings inhibited (rin) mutants and in the early stages of ripening of normal lines (Tucker et al. 1980; Brady et al. 1983; Knegt et al. 1988). Under denaturing conditions PG1 contains polypeptides that appear to be identical to PG2A and PG2B and a smaller polypeptide (Moshrefi and Luh 1983). There are suggestions that PG1 is formed from PG2 by interaction with either a specific glycopeptide (Pressey 1984; Knegt et al. 1988) or carbohydrate (Tucker et al. 1981). Alternative theses on PG1's role include: that it is the active in vivo isoform (Tucker et al. 1981; Knegt et al. 1988), that the second polypeptide in PG1 may bind and site PG onto the cell wall (Brady et al. 1987) and that PG1 does not exist in vivo but is formed when PG2 is co-extracted with a nonspecific 'convertor' glycoprotein (Pressey 1986, 1988).

PG1 is notably thermostable (Tucker et al. 1981; Moshrefi and Luh, 1983). The thermostability makes it important as a catalyst of polymer changes when tomato fruit are processed and it is an important determinant of the heat input required for processing. For this reason, and because of the possibility that PG1 is the form of the enzyme active in vivo there is commercial interest in the genetic regulation of the content of PG1 in tomato fruit. Knowledge of the structure and in particular, the amino acid sequence of the subunit could allow the gene sequence to be sought. Genetic manipulation using antisense or transgene technology could follow.

The present inventors have, for the first time, developed practical methods for isolating the protein PG1 and each of its subunits. The chemistry of the two subunits is described and N-terminal and some internal sequence of the second or β-subunit of PG1 is described herein for the first time.

SUMMARY OF THE PRESENT INVENTION

In a first aspect the present invention consists in an isolated DNA sequence which encodes at least part of the tomato enzyme endopolygalacturonase PG1 β-subunit.

In a second aspect the present invention consists in a DNA sequence which encodes at least part of the tomato enzyme endopolygalacturonase PG1 β-subunit, the DNA sequence being flanked by at least one heterologous DNA sequence 5' to or 3' to said endopolygalacturonase PG1 β-subunit encoding sequence.

In a preferred embodiment of the present invention the DNA sequence encodes a polypeptide which includes the following amino acid sequence:
E-K-H-S-G (SEQ ID NO: 1)
or a functional equivalent thereof.

In a preferred embodiment of the present invention the DNA sequence encodes a polypeptide which includes the following amino acid sequence:
E-K-H-S-G-D-I-H (SEQ ID NO: 2)
or a functional equivalent thereof.

In a further preferred embodiment of the present invention the DNA sequence encodes a polypeptide which includes the following amino acid sequence:
E-K-H-S-G-D-I-H-G-A-T-Y-S-D-K (SEQ ID NO: 3)
or a functional equivalent thereof.

In a further preferred embodiment of the present invention the DNA sequence encodes a polypeptide which includes the following amino acid sequence:
D-A-N-D-I-E-A-N-T-Y-N-Y-G-Q-X-P-N-E-G (SEQ ID NO: 4)
or a portion thereof or functional equivalent thereof.

In a further preferred embodiment of the present invention the DNA sequence encodes a polypeptide which includes the following amino acid sequence:
A-L-N-A-E-N-Q-V-R-I-K (SEQ ID NO: 5)
or a portion thereof or functional equivalent thereof.

In yet a further preferred embodiment of the present invention the DNA sequence encodes a polypeptide the N-terminal amino acid sequence of which is as follows:
E-K-H-S-G-D-I-H-G-A-T-Y-S-D-K (SEQ ID NO: 6)
or a portion thereof or functional equivalent thereof, and in which the polypeptide includes the following amino acid sequence(s):
D-A-N-D-I-E-A-N-T-Y-N-Y-G-Q-X-F-N-E-G
and/or
A-L-N-A-E-N-Q-V-R-I-K
or a portion(s) thereof or functional equivalent(s) thereof.

In a preferred embodiment of the present invention the heterologous DNA sequence is either a constitutive or inducible promoter. A preferred constitutive promoter is the CaMV 35S promoter whilst a preferred inducible promoter is the alcohol dehydrogenase promoter.

Amino acid sequences are stated using the I.U.P.A.C. one-letter code abbreviations for amino acid residues, defined as follows:

G-Glycine, A-alanine, V-valine, L-lysine, I-isoleucine, S-serine, T-threonine, D-aspartic acid, E-glutamic acid, N-asparagene, Q-glutamine, K-lysine, H-histidine, R-arginine, F-phenylalanine, Y-tyrosine, W-tryptophan, C-cystene, M-methionine and P-proline.

In addition, the symbol "X" is used to indicate an unknown amino acid residue.

The phrase "functional equivalents thereof" is intended to cover peptides which have a slightly altered amino acid sequence from that set out above, but which retain substantially the same biological activity. This may be achieved by various changes, such as insertions, deletions and substitutions, either conservative or non-conservative where such changes do not substantially alter the biological activity of the peptide. By conservative substitutions the intended combinations are:

G, A; V, I, L, M; D, E; N, Q; S, T; K, R, H; and F, Y, W.

In yet a further aspect the present invention consists in a DNA construct comprising the DNA sequence of the present invention, the DNA sequence being joined in the opposite orientation for expression 5' to the 3' terminus of a transcriptional initiation region functional in tomatoes.

In a further aspect the present invention consists in a genetically engineered tomato plant containing the DNA construct of the present invention.

BRIEF DESCRIPTION OF THE DRAWINGS

In order that the nature of the present invention may be more clearly understood, preferred forms thereof will now be described with reference to the following examples and accompanying drawings in which:

FIGS. 2A, 2B and 2C The UV spectra of (a) PG2A in 20 mM MES, 200 mM NaCl, 0.1 mM DTT pH6.0; (b) PG1 in 50 mM phosphate, 400 mM NaCl, 0.1 mM DTT pH6.0; (c) β-subunit of PG1 in 6 M urea, 50 mM phosphate, 300 mM NaCl, 1 mM DTT pH6.0. Spectra are adjusted for solvent absorption.

FIGS. 4A and 4B (A) The separation of the subunits of PG1 on a Mono S HR 5/5 column with a linear gradient of 75 to 500 mM NaCl in 50 mM phosphate, 6 M urea, 1 mM DTT, pH 6.0. (B) Identification by SDS—polyacrylamide gel electro phoresis, of the subunit composition of PG1 and of peak 1 and peak 2 from the Mono S column as shown in (A).

A. The pericarp from a fruit was divided into 10 g portions, each portion was heated for differing time periods, then extracted in 1.5 M NaCl buffer and assayed for total PG activity (Pogson 1991).

Two replicates, fruit A (▲) and fruit B (o) were undertaken.

Fruit A:
plot 1, y=146–9.03x, $R^2$=94.1%, p<0.001
plot 2, y=71.6–1.11x, $R^2$=82.9%, p=0.001

Fruit B:
plot 1, y=115–8.7x, $R^2$=99.9%, p=0.001
plot 2, y=23.7–0.28x, $R^2$=89.3%, p<0.001

B. Typical temperature profile of the pericarp portions. The temperature was monitored by thermocouples.

Figure 6:
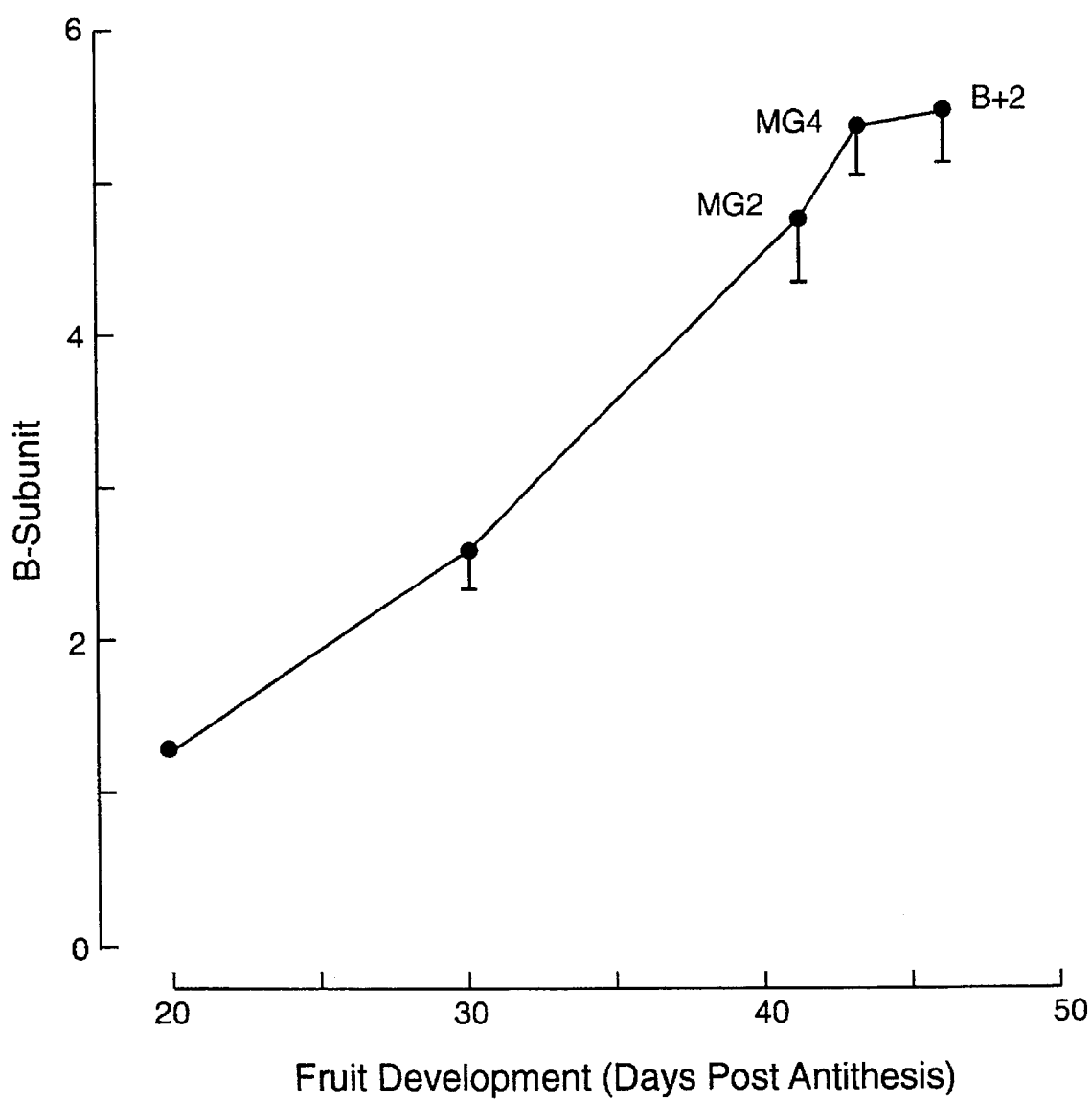

FIG. 6 Accumulation of the β-subunit during development

A. Western blot of the cross-reactivity of antibody to the β-subunit with protein extracts from developing fruit of the tomato cv. de Ruiter 83G38 was scanned densitometrically. The amount of β-subunit was determined by the amount of absorbance of the antibody reaction product at $M_r$ 37,000, 39,000 and 41,000. The units were an average of the area under the absorbance for each stage of development. Equivalent dry weights were used for each stage of development. MG2—mature green fruit immediately prior to increased ethylene production associated with ripening. MG4—mature green fruit in which ethylene production has risen sharply from basal (ca. 0.6±0.2 $nLg^{-1}$ per h) to ca. 3.5±1.0 $nLg^{-1}$ per h, and carotenoid pigment is evident in the interior of the fruit. B+2—is two days after the "Breaker" stage, which is the stage at which the color change on the exterior of the fruit is first evident.

DETAILED DESCRIPTION OF THE INVENTION

METHODS

PG1 Purification

Pericarp tissue from red ripe fruit of the processing tomato, Heinz 2605, was soaked for 3 hours in 0.1% sodium metabisulfite at 2° C. and than rinsed for 48 hours in cold, running water. Excess water was removed from the residue before it was homogenized in 100 mM sodium citrate, 5.5 M NaCl, 40 mM β-mercaptoethanol, pH4.0 (equal W/V). The homogenate was left overnight at 220 C. before centrifuging at 16,300 g for 50 min. The supernatant was concentrated to 200 ml by ultrafiltration (STY30 cartridge, Amicon Scientific) diluted with 100 mM citrate pH4.0 to reduce the NaCl concentration to 200 mM and reconcentrated. The concentrate was clarified by centrifuging at 27,000 g for 60 min, and applied to a S-Sepharose FF column (Pharmacia LKB Biotechnology) 25×250 mm, equilibrated with 100 mM citrate, 200 mM NaCl, 0.1 mM DTT, pH4.0. Bound proteins were eluted with a concave gradient to 1500 mM NaCl in 100 mM citrate, 0.1 mM DTT, pH4.0. PG2 was the first peak of PG activity to elute and PG1 was the second peak. Active fractions of PG1 were pooled, concentrated by ultrafiltration, dialysed against 50 mM phosphate, 200 mM NaCl, 0.1 mM DTT, pH6.0 (start buffer) and applied to a FPLC Mono S HR 10/10 column (Pharmacia) equilibrated with the start buffer. The enzyme was eluted using a linear gradient of NaCl to 1000 mM and loaded on to a Concanavalin A-Sepharose 4B (Pharmacia) column, 25×100 mm in 50 mM sodium phosphate buffer, 500 mM NaCl, 1 mM $MgCl_2$, 1 mM $CaCl_2$ pH6.0. Unbound proteins were washed from the column before PG1 was eluted using a gradient of buffer containing from 0–200 mM α-methylamannoside. Active fractions were pooled and concentrated; 2 ml was applied to a column of Sephacryl 300 HR (Pharmacia), 25×800 mm, in 50 mM phosphate, 500 mM NaCl, 0.1 mM DTT pH6.0. Fractions with PG1 activity were concentrated by ultrafiltration, diluted to 200 mM NaCl and fractionated on a Mono S HR 5/5 column using a linear gradient of NaCl in 50 mM phosphate, 0.1 mM DTT pH6.0.

Separation of the Subunits of PG1

PG1 was incubated in dissociating buffer (50 mM phosphate, 75 mM NaCl, 10 mM DTT, 6 M Urea, pH6.0) overnight in an atmosphere of nitrogen at 20° C. Subunits were separated on a Mono S HR 5/5 column using a linear gradient of NaCl to 500 mM in 50 mM phosphate, 6 M urea, 1 mM DTT pH6.0. The separate subunits were concentrated by ultrafiltration using a YM10 (Amicon Scientific) membrane and rechromatographed under the same conditions, except at pH4.0.

Amino Acid Analysis

Prior to amino acid analysis or protein sequencing, proteins were reduced and carboxymethylated as described by Sheehy et al. (1987). Proteins were hydrolysed in 6 M HCl for 24 h in a nitrogen atmosphere. The phenylisothiocyanate derivatives of the released amino acids were analysed by the method of Heinrikson and Meredith (1984). N-terminal protein sequences were determined on a gas phase protein sequencer (Applied Biosystems Model 470A).

Sequencing

N-terminal sequencing on PG1 protein was carried out after carboxymerthylation by the methods described by Sheehy et al (1987). The sequence of the second subunit was deduced from the double sequence of the PG1 protein and the known N-terminal sequences of the PG2 subunit. The N-terminal sequences were confirmed by sequencing the subunits individually after they had been separated by ion-exchange chromatography in 6 M urea. The second or β-subunit was carboxymethylated and, suspended in 0.1 M Tris, 0.1% SDS pH8.35 digested with endoproteinase lys-C (Boehringer—Mannheim Gmb H3) at 40° C. for 2 h. After centrifuging, peptides in the supernatant were separated using a Brownlea C18 RP, 5u, 4.6–250 mm column and a gradient of 0–2 h 70% acetonitrile in 0–1% TFA.

Endopolygalacturonase I is an in vivo entity

PG2 and the beta-subunit can combine in vitro to form PG1 or a PG1-like compound (Pressey, 1988; Knegt et al., 1988). This raises the possibility that PG1 in extracts results from the co-extraction of the two polypeptides and their combination in the extraction fluid (Pressey, 1988). Critical examination of the evidence for and against the existence of PG1 in situ in cell walls leads to the conclusion that the evidence is ambiguous. This is the case when the tissue is disrupted, or extracts are made.

Figure 5A:
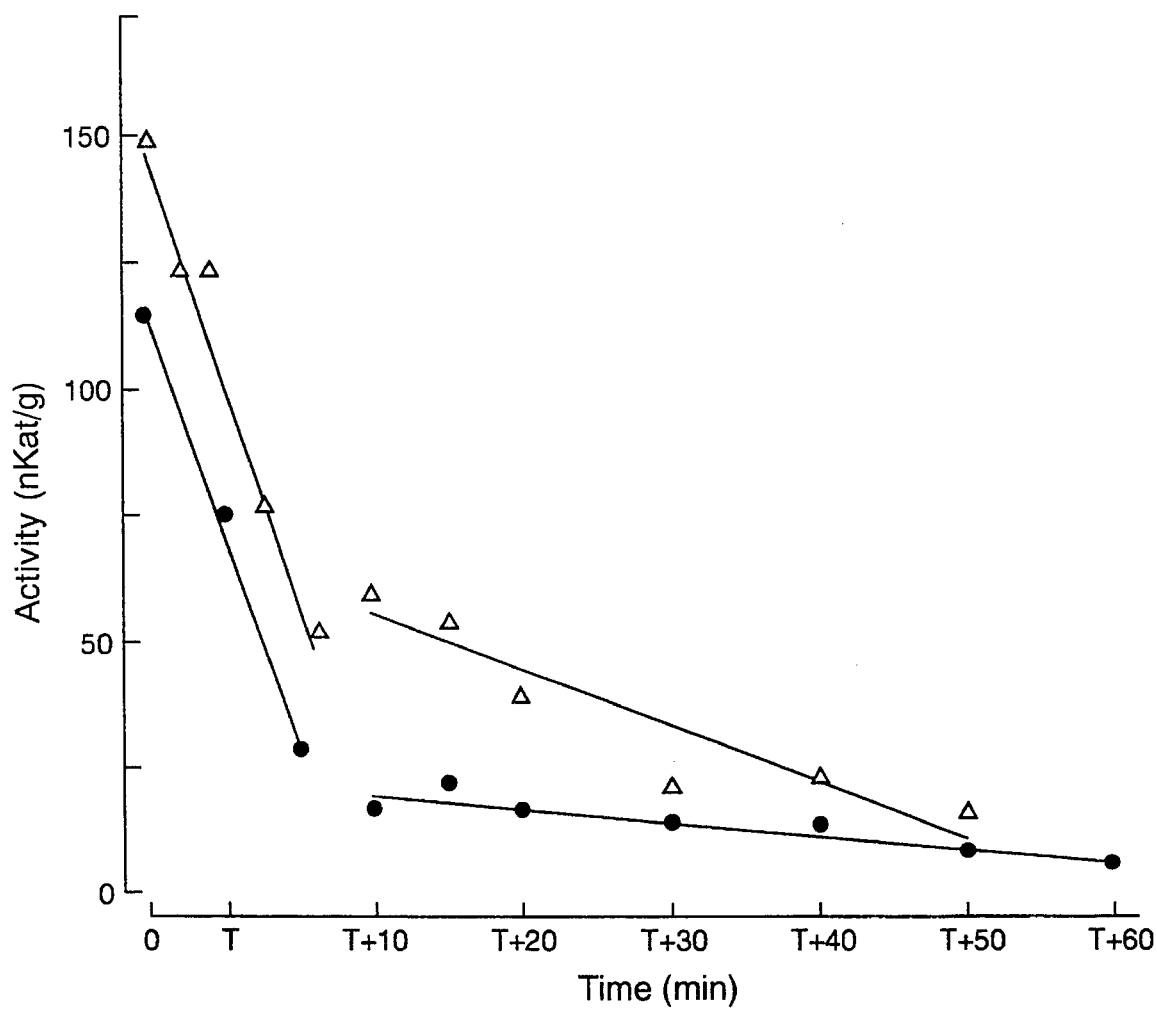
FIGS. 5A and 5B Inactivation of PG activity in pericarp at 60° C.
Figure 5B:
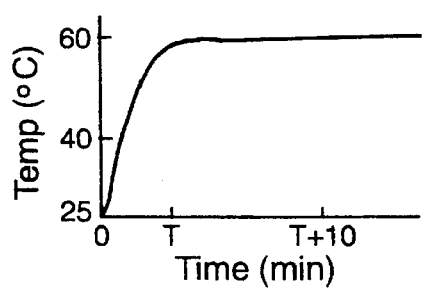

Since PG1 is more resistant to heat than PG2, this property can be used to investigate the presence of PG1 in tissues provided the heat can be applied without the tissue losing its structural integrity. The inactivation of the polygalacturonase enzyme activity was investigated in intact fruit heated to 60° C. A biphasic decay in activity was measured exactly as predicted from the proportions of PG1 and PG2 in extracts of the tissues (FIG. 5). This is strong evidence that PG1 exists as such in the tissue and that polygalacturonase activity in situ is mediated by an enzyme with the characteristics of PG1.

Distribution of the beta-subunit in tomato plants

Antibodies were raised in New Zealand white rabbits to purified PG1 protein. Each rabbit was injected subcutaneously with 1 mg of antigen emulsified with Freund's Complete Adjuvant. Booster injections were made after 28 days, and blood samples were taken after a further 7 days. The blood was clotted and centrifuged, and the serum treated with ammonium sulphate to 40% of saturation to remove albumins. Precipitation was repeated once and the supernatant dialysed against phosphate buffered saline. The serum was affinity purified (Goding, 1986) by binding to PG2 coupled to Sepharose 4B (Pharmacia). Unbound IgG was washed from the column with phosphate-buffered saline and the bound fraction with 0.1 M acetic acid; the bound fractionj was neutralised and dialysed against phosphate-buffered saline. The process of binding to a PG2 affinity column and elution was repeated once.

The affinity-purified anti-PG1 serum recognised native PG1 but not PG2 protein; on Western blots (Kyhse-Anderson, 1984; Bjerrum and Schafer-Nielsen, 1986) it recognised the beta subunit.

Total protein extracts were made from tomato tissues in 50 mM sodium phosphate, 5% SDS, 6 M urea, 5% glycarol, 10% beta-mercaptoethanol pH 6.0 and the extracted proteins separated through polyacrylamide gels in the presence of SDS. The separated proteins were blotted to nitrocellulose and probed with the purified anti-PG1 antisera. The beta-subunit antigen was detected in fruit pericarp tissue, but not in locule tissue or non-fruit tissues. In fruit pericarp, the antigen was detected 30 days but not 15 days post-anthesis. FIG. 6 shows its concentration relative to dry matter in the pericarp of developing fruit of the cultivar de Ruiter 83G38.

RESULTS

The purification of PG1

By avoiding $(NH_4)_2SO_4$ precipitation and dialysis in buffers of low ionic strength, PG1 was purified from fruit of the processing line Heinz 2605 (Table 1). Overall purification was about 109-fold and the yield about 10%. The strong affinity of PG1 for cation exchange columns and for the lectin, Concanavalin A, aided purification.

PG1 Structure

Figure 1:
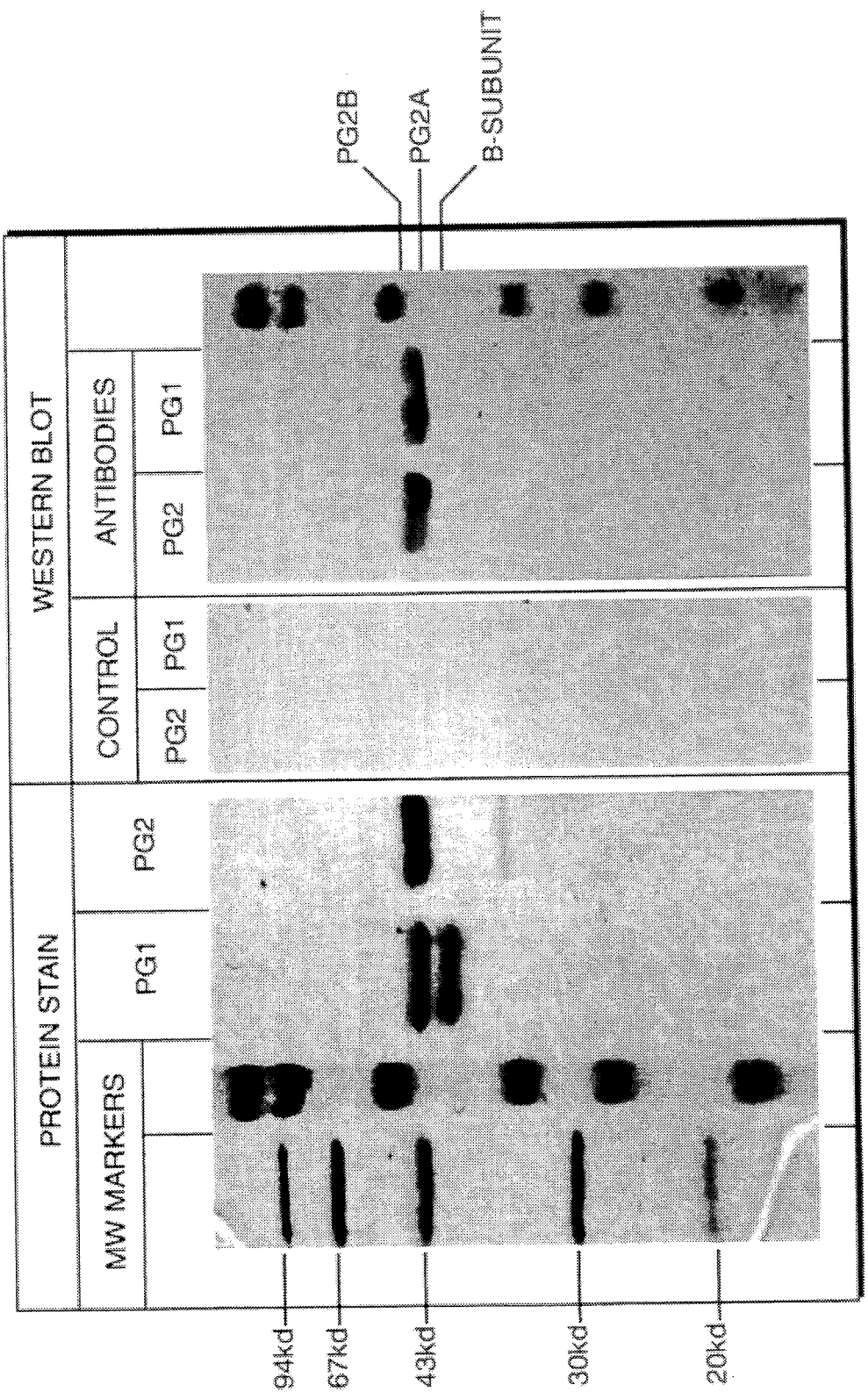
FIG. 1 PG1 and PG2 examined by SDS-gel electrophoresis and immunologically on a nitrocellulose blot. Lane 1 is a protein series for Mr calibration; lanes 2 and 9 are prestained Mr standards; lanes 3, 6 and 8 carry purified PG1 and lanes 4, 5 and 7 a mixture of PG2A and 2B. Lanes 1 to 4 were stained with Coomassie brilliant blue R; lanes 5 and 6 were exposed to a non-specific rabbit serum and lanes 7 to 9 to the serum of a rabbit inoculated with PG2A; lanes 5 to 9 were then treated with a conjugate of horseradish peroxidase and goat-anti-rabbit IgG and the peroxidase assayed.
Figure 3A:
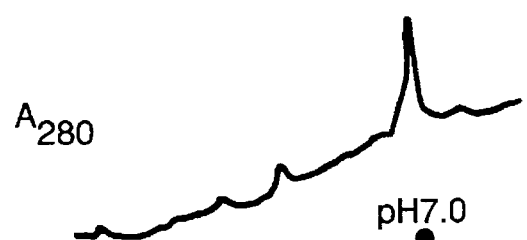
FIGS. 3A, 3B, 3C and 3D The fractionation of PG1 and PG2 by chromatofocusing on a Pharmacia MonoP HR 5/20 column. Proteins were loaded in 0.02 M ethanolamine and the column was eluted at 0.5 mL min-1. The elution sequence was 4 min 0.025 M ethanolamine, and then a linear gradient 0 to 100 over 120 min to a buffer containing 20 ml "polybuffer 96" plus 20 ml "polybuffer 74" in 200 ml adjusted with HCl to pH5. Fractions (4 min) were assayed for pH and enzyme activity; the eluate was monitored for protein ($A_{280nm}$). (A) Protein and (B) enzyme activity in eluate of column loaded with PG1. (C) Protein and (D) enzyme activity in eluate of column loaded with PG2.
Figure 3B:
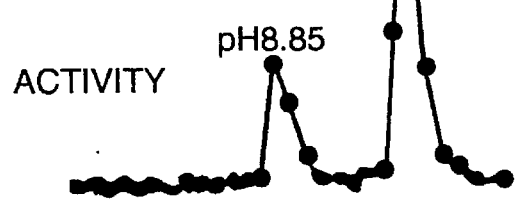
Figure 3C:
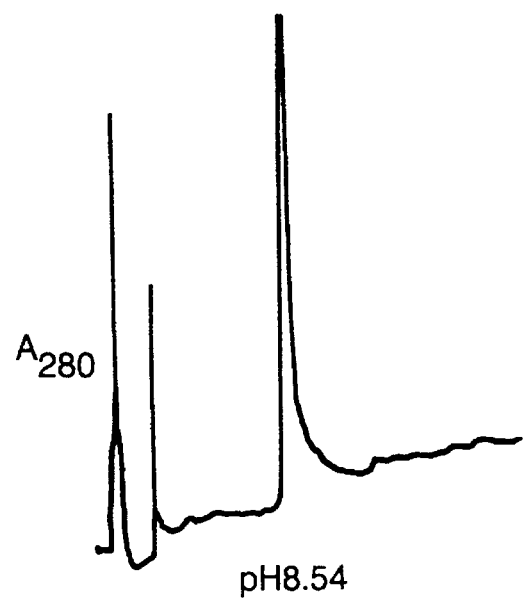
Figure 3D:
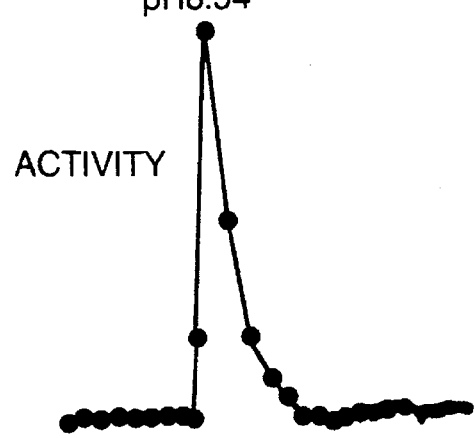

Purified PG1, when reduced with β-mercaptoethanol and denatured with SDS separated into three polypeptides of Mr 45 K, 43 K and 39 K as estimated by SDS-polyacrylamide electrophoresis (FIG. 1). A similar observation was made by Moshrefi and Luh (1983). The 45 K and 43 K, but not the 38 K polypeptides bound antiserum to PG2A, indicating that the smaller polypeptides was a distinct and different subunit of the PG1 molecule (FIG. 1).

The smaller 39 K subunit, here termed the β-subunit, was shown to be chemically distinct. Purified samples of PG1 and PG2 were dialyzed against $NH_4HCO_3$, lyophilized and analyzed for carbohydrate (Table 2). Both proteins contained glucosamine, mannose, xylose and fucose, but relative to the polypeptide, the carbohydrate content of PG1 was higher (18. 9%) than that of PG2 (11.2%). Since the larger subunits of PG1 are equivalent in size to PG2A and PG2B, the extracarbohydrate in PG1 is likely to be within the β-subunit. It was confirmed that the β-subunit stained intensely with Schiff's reagent (result not shown). The UV spectra of purified samples of PG1 and PG2 are shown in FIG. 2. PG1 has an absorption maximum about 275 nm and PG2 about 280 nm indicating that PG1 has the higher ratio of tyrosine to tryptophane. The relatively high content of tyrosine in PG1 was confirmed by amino acid analysis (Table 3).

PG1 and PG2 are separable by chromatofocusing (FIG. 3) and it was confirmed (Ali and Brady, 1982) that, although PG1 elutes after PG2 during cation exchange chromatography, PG1 has the lower isoelectric point. This suggested that the β-subunit is more acidic than PG2. When PG1 was denatured in 6 M urea, 50 mM sodium phosphate, 75 mM NaCl, 10 mM DTT pH6.0, two polypeptides were separable by cation exchange chromatography (FIG. 4). The less tightly bound polypeptide corresponded to the β-subunit and the more tightly bound to PG2 as shown by SDS-polyacrylamide gel electrophoresis (FIG. 4). The spectrum of the recovered presumptive β-subunit (FIG. 2) and its amino acid analysis (Table 3) showed a high content of tyrosine.

On the basis of the amino acid analysis and the apparent molecular size, it was suggested that the β-subunit polypeptide was of Mr 28, 120 and contained 21 moles/mole of tyrosine. Spectral analysis of the peptide in guanidine-HCl (Edelhoch, 1967) showed the presence of 1 mole/mole of tryptophane giving the polypeptide of Mr of 28,342. Allowing that PG1 contains 1 mole each of PG2 and the β-subunit, it is calculated from the analysis in Tables 2 and 3, that the β-subunit has 27.9% by weight of carbohydrate and a Mr of 39,250. PG2 had a polypeptide weight of 40,279 (Sheehy et al. 1987) and, from Table 2, 5075 g per mole of carbohydrate to give a subunit of 45,354. Again assuming 1 mole/mole of each subunit, the molecular mass of PG1 would be 84,600 (Table 3).

The assumption of 1 mole each of the β-subunit and of PG2 in PG1 is not immediately consistent with the 3 subunits shown in FIG. 1. If the 43 K and 45 K components of PG1 represent the PG2A and PG2B forms of PG2 (Ali and Brady 1982), and their recognition by specific antisera would suggest this, then it seems likely that PG1 is a population of related molecules containing either PG2A or PG2B linked with the β-subunit.

The evidence is not entirely consistent with PG1 having a 1:1 mix of the β-subunit of PG2. Based on the tyrosine, tryptophane and cysteine contents, an absorption ratio, 280 nm to 288 nm of 1.74 was expected for PG1 but a ration of 1.695 was observed. Recoveries of the subunits after cation exchange chromatography in urea was close to a molar ratio of 1.2:1 for PG2: β-subunit. It is clear that PG2 and the β-subunit are major components of PG1 but more detailed analyses are required to define the structure.

Amino Acid Sequence

The N terminal of the PG2 subunit of PG1 was identical to that already described for the free PG2 protein (Sheehy et al, 1987). The N-terminal sequence of the second or β-subunit was determined by difference from the sequences from the composite PG1, and from the unique sequence of the separated β-subunit. From several analysis the sequence emerged as:

E-K-S-G-D-I-H-G-A-T-Y-S-D-K-
Two internal peptides were sequenced:
-D-A-N-D-I-E-A-N-T-Y-N-Y-G-Q-X-F-N-E-G-
-A-L-N-A-E-N-Q-V-R-I-K-
The latter sequence is of particular interest because of its homology with the 250–260 region of PG2 sequence -I-G-A-E-N-G-V-R-I-K-T-W-Q There is much circumstantial evidence for the thesis that the PG1 isoform of endopolygalacturonase is involved in the initial catabolism of pectic polymers in ripening tomato fruits. The PG1 isoform is the only form of the enzyme recovered from tissue when softening is initiated. The present inventors have demonstrated that PG1 (more than PG2) has the capacity, in vitro at least, to hydrolyse polygalacturonic substances in the low ionic conditions that may prevail in the fruit apoplast. 'Nr' mutant fruit and PG transgenic 'rin' fruit have pectins with modified solubility (Seymour et al. 1987; Giovannoni et al. 1989) and PG exclusively as the PG1 isomer (Tucker et al. 1980; Bennett, private communication; Brady et al. 1983). Homozygous nor and rin fruit have no PG and the pectin solubility remains unchanged (Seymour et al. 1987). Circumstantially rhen, there is a link between the presence of PG1 and changes in the pectin polymers, and PG1 has the capacity to modify extracted pectin polymers.

This circumstantial association is well short of proof that PG1 occurs and is active in vivo, but is sufficient to lead to an enquiry of the nature of the PG1 and the significance of the differences between PG1 and PG2. Since characterization of the PG1 converting factor(s) has proved elusive the present inventors have dissociated the native PG1 protein, isolated and partially characterised its subunits. Characterising the actual components of PG1 will lead towards identifying the putative converting factor(s) and elucidation of the process of PG1 formation.

The present inventors have successfully isolated and partially characterised the β-subunit of PG1. They have also added to the evidence that the PG2-like subunits of PG1 are indeed identical to PG2 by establishing that N-terminal sequence of PG2 is present in PG1. The other major component of PG1, the β-subunit, is a heavily-glycosylated, rather acidic polypeptide rich in glycine and tyrosine. The carbohydrate is present as N-linked N-acetylglucosamine, mannose, fucosa and xylose chains such as are common in plant glycoproteins (Ashfor, 1987). Although it is necessary to have reducing agents present to separate the PG1 subunits in dissociating solvents, there is as yet no evidence that disulfide bonds couple the subunits. Indeed the presence of cysteine residues in the β-subunit has not been demonstrated.

Sequence information on the β-subunit polypeptide is presented here for the first time. A molecular characterisation of the β-subunit should lead to probes that will enable its role through development to be evaluated and any role it has in siting or regulating PG action to be revealed.

The sequence of the PG subunit opens the way to the isolation and sequencing of its gene. From the amino acid sequence a putative nucleic acid (RNA or DNA) can be synthesised and used (a) as a probe for use on cloned DNA towards isolating the gene and (b) as template for use, with RNA preparations, for production of cDNA using the PCR technique. Recovery of either gene or cDNA segments would rapidly lead to an extension of the sequence information with the ability to alter gene expression by antisense suppression of the steady state mRNA level in fruit. It may also be possible to use the putative nucleic acid sequence (derived from the partial protein sequence) directly as an antisense agent. For example, antisense genes may include sequence (s) coding for catalytic region(s) of riboendonucleases.

The introduction of the antisense gene into tomato fruit is a well established technique (Sheehy et al. 1988; Smith et al. 1988; Hamilton et al 1990). The antisense gene is formulated behind a viral promoter. It is introduced into tomato cotyledon tissue via a transformation vector utilising *Agrobacterium tumefaciens* (Fillatti et al 1987). Plants are regenerated from the transformed tissue. The viral promoter ensures that the antisense element is expressed strongly and contitutively in the regenerated plant. Alternatively, if expression is to be limited for example to fruit, a tissue specific promoter (Giovannoni et al 1989) may be used.

The catalytic subunit of tomato fruit endopolygalacturonase has been suppressed by the antisense approach (Sheehy et al, 1988, Smith et al. 1988) with positive effects on fruit quality, especially for processing. When the total amount of endopolygalacturonase is limited, most of it is in the thermostable PG1 form. To prevent this enzyme causing an excessive degradation of pectin during processing, a "hot break" procedure must be used with attendant increases in energy costs. If the content of PG1 could be reduced, the "cold break", low cost processing system would be applicable. Use of the PG1 second subunit gene in the antisense form should result in a reduction in PG1 with a consequential improvement in the processed fruit. It is possible that the unprocessed fruit would retain firmness for a longer period for there is some evidence that PG1 is the form of endopolygalacturonase that is active within the fruit (Ostaryoung et al, 1990).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 2-continued

| COMPONENT | SAMPLE | |
|---|---|---|
| | PG1 | PG2 |
| | (ug/mg polypeptide**) | |
| Mannose | 91.0 ± 1.7 | 44.0 ± 0.2 |
| X* | 15.0 ± 0.2 | |
| Glucosamine | 71.7 ± 3.1 | 62.4 ± 3.5 |

*This unknown has a retention time, relative to inositol of 0.64
**Measured spectrophotometrically, allowing for differing extinction coefficients.

Figures are means with half the range from two independent analyses.

TABLE 3

AMINO ACIDS IN PG2A, PG1 AND PG1 β-SUB-UNIT PG2A$^2$
Molar Ratios Moles per Mole of Isoleucine
(Moles per Mole Polypeptide)

| | PG2A | PG1 | β-SUB-UNIT | PG2A$^2$ | β-SUBUNIT$^3$ |
|---|---|---|---|---|---|
| Asp(n) | 1.28$^1$ | (1.50)$^4$ | 2.54$^1$ | 7.23$^1$ | 54 | 52 |
| Glu(n) | 0.85 | (0.98) | 1.09 | 2.76 | 34 | 20 |
| Ser | 0.99 | (1.08) | 1.53 | 3.26 | 39 | 25 |
| Gly | 0.93 | (0.86) | 1.85 | 5.13 | 31 | 38 |
| His | 0.16 | (0.16) | 0.29 | 0.73 | 6 | 6 |
| Arg | 0.22 | (0.19) | 0.33 | 0.86 | 7 | 6 |
| Thr | 0.53 | (0.58) | 1.18 | 2.79 | 21 | 21 |
| Ala | 0.64 | (0.64) | 0.96 | 2.49 | 23 | 19 |
| Pro | 0.49 | (0.36) | 0.66 | 1.26 | 13 | 10 |
| Tyr | 0.21 | (0.28) | 0.77 | 2.79 | 10 | 21 |
| Val | 0.81 | (0.86) | 1.07 | 1.63 | 31 | 13 |
| Met | 0.10 | (0.08) | 0.09 | 0.06 | 3 | 1 |
| Cys | 0.26 | (0.39) | 0.31 | ND | 14 | |
| Ile | 1.00 | (1.00) | 1.00 | 1.00 | 36 | 7 |
| Leu | 0.51 | (0.47) | 0.57 | 0.26 | 17 | 2 |

TABLE 1

PURIFICATION OF PG1 FROM RIPE TOMATO FRUIT

| FRACTION | PG1 | | | SPECIFIC PURIFICATION | |
|---|---|---|---|---|---|
| | PROTEIN (mg) | ACTIVITY (ukat) | YIELD (%) | ACTIVITY (ukat mg-1) | FACTOR |
| 0.3M NaCl Extract | 8800 | 0 | 0 | 0 | 1$^A$ |
| 1.5M NaCl Extract | 1278 | 109 | 100 | 0.085 | 8 |
| S-Sepharose, pH4 | 141 | 68 | 62 | .268 | 24 |
| Mono S, pH6 | 50 | 46 | 42 | .92 | 84 |
| Con A | 38 | 41 | 38 | 1.08 | 98 |
| Sephacryl 300 HR | 25 | 28 | 26 | 1.12 | 102 |
| Mono S, pH6 | 10 | 12 | 11 | 1.2 | 109 |

Periocarp weight fractionated - 5 kg
$^A$From tissue, purification is 109 fold, because 8.8 g of protein without PG1 activiity is discarded in the preliminary extractions.

TABLE 2

| COMPONENT | SAMPLE | |
|---|---|---|
| | PG1 | PG2 |
| | (ug/mg polypeptide**) | |
| Fucose | 28.3 ± 0.9 | 8.1 ± 0.1 |
| Xylose | 27.7 ± 0.6 | 10.6 ± 0.4 |

TABLE 3-continued

AMINO ACIDS IN PG2A,
PG1 AND PG1 β-SUB-UNIT PG2A[2]
Molar Ratios Moles per Mole of Isoleucine
(Moles per Mole Polypeptide)

|     | PG2A | PG1    | PG1  | β-SUB-UNIT | PG2A[2] | β-SUBUNIT[3] |
|-----|------|--------|------|------------|---------|--------------|
| Phe | 0.45 | (0.36) | 0.42 | 0.25       | 13      | 2            |
| Lys | 0.92 | (0.72) | 1.07 | 1.77       | 26      | 14           |
| Trp |      | (0.11) |      |            | 4       | 11[5]        |

[1]By direct analysis
[2]From the sequence (Sheehy et al. 1987)
[3]Assumes polypeptide molecular mass of 27,342 for subunit
[4]Calculated from the sequence (Sheehy et al. 1987)
[5]Measured spectrophotometrically

REFERENCES

Ali, Z. M. and Brady, C. J. Purification and characterization of the polygalacturonases of tomato fruits. Aust. J. Plant Physiol. 9, 155 1982.

Ashford, D., Dwek, R. A., Welply, J. K., Amatayakul, S., Homans, S. W., Lis, H., Taylor, G. N., Sharon, N. and Rademacher, T. W. The β-1-2D-xylose and α-1-3-1-3-L-fucose substituted N-linked oligosaccharides from *Erythrina cristacalli* lectin. Isolation, characterization and comparison with other legume lectins. Eur. J. Biochem. 166, 311, 1987.

Bird, C. R., Smith, C. J. S., Ray, J. A., Moureau, P., Bevan, M. W., Bird, A. S., Hughes, S., Morris, P. C., Grierson, D. and Schuch, W. The tomato polygalacturonase gene and ripening—specific expression in transgenic plants. Plant Mol. Biol. 11, 651, 1988.

Bjerrum, O. J., and Schafer-Nielsen, C. (1986) Buffer systems and transfer parameters for semidry electroblotting with horizontal apparatus. in Dunn, M. J. (ed.): Electrophoresis '86. Weinheim: VCH, pp, 39–41.

Brady, C. J., MacAlpine, G., McGlasson, W. B. and Ueda, Y. Polygalacturonase in tomato fruits and the induction of ripening. Aust. J. Plant Physiol. 9, 171, 1982.

Brady, C. J., Meldrum, S. K., McGlasson, W. B. and Ali, Z. M. Differential accumulation of the molecular forms of polygalacturonase in tomato mutants. J. Food Biochem. 7, 7, 1983.

Brady, C. J., McGlasson, W. B. and Speirs, J. (1987). The biochemistry of fruit ripening. In: Tomato Biotechnology. Plant Biology 4, 279, 1987. (Eds D. J. Nevins, R. A. Jones) (Alan R. Liss Inc: N.Y.).

DellaPenna, D., Alexander, D. C. and Bennett, A. B. Molecular cloning of tomato fruit polygalacturonase: analysis of polygalacturonase mRNA levels during ripening. Proc. Natl Acad. Sci. USA 83, 6420 1986.

DellaPenna, D., Lincoln, J. E., Fischer, R. L. and Bennett, A. B. Transcriptional analysis of polygalaturonase and other ripening associated genes in Rutgers, rin nor and Nr tomato fruit. Plant Physiol. 90, 1372, 1989.

Edelhoch, H. Spectroscopic determination of tryptophan and tryosine in proteins. Biochemistry 6, 1946, 1967.

Fillatti, J. J., Kiser, J., Rose, B. and Commie, L., Efficient transformation of tomato and the introduction and expression of a gene for herbicide tolerance. In Tomato Biotechnology, D. J. Nevis and R. A. Jones, eds. (N.Y.: Alan R. Liss) 199, 1987.

Giovannoni, J. J., DellaPenna, D., Bennett, A. B. and Fisher, R. L. Expression of a chimeric polygalacturonase gene in transgenic rin (Ripening Inhibitor) tomato fruit results in polyuronide degradation but not fruit softening. The Plant Cell 1, 53, 1989.

Goding, J. W. (1986). Monoclonal antibodies: principles and practice. Sydney: Academic Press.

Grierson, D. Gene expression in ripening tomato fruit. Critical Reviews in Plant Science. 3, 113, 1985.

Grierson, D., Tucker, G. A. Keen, J., Ray, J., Bird, C. R. and Schuch, W. Sequencing and identification of a cDNA clone for tomato polygalacturonase. Nucleic Acids Res. 14, 8595, 1986.

Hamilton, A. J., Lycett, G. W. and Grierson, D., Antisense gene that inhibits synthesis of the hormone ethylene in transgenic plants. Nature 346, 284, 1990.

Heinrickson, R. L. and Meredith, S. C. Amino acid analysis by reverse phase high performance liquid chromatography: precolumn derivatization with phenylisothiocyante. Anal. Biochem. 136, 65, 1984.

Knegt, E., Varmeer, E. and Bruinsma, J. Conversion of the polygalacturonase isoenzymes from ripening tomato fruits. Physiol. Plant 72, 108, 1988.

Khyse-Anderson, J. (1984) Electroblotting of multiple gels: a simple apparatus without buffer tank for rapid transfer of proteins from polyacrylamide to nitrocellulose. J. Biochem. and Biophys. methods 10, pp 203–209.

Maunders, M. J., Holdsworth, M. J., Slater, A. K., Knapp, J. E., Bird, C. R., Schuch, W. and Grierson, D. Ethylene stimulates the accumulation of ripening related messenger RNAs in tomatoes. Plant Cell Environ. 10, 177, 1987.

Moshrefi, M. and Luh, B. S. Carbohydrate composition and electrophoretic properties of tomato polygalacturonase isoenzymes. Eur. J. Biochem. 135, 511, 1983.

Osteryoung, K. W., Toenjes, K., Hall, B., Winkler, V. and Bennett, A. A. Analysis of tomato polygalacturonase expression in transgenic tobacco. The Plant Cell, 2, (1239), 1990.

Pressey, R. Purification and characterization of tomato polygalacturonase converter. Eur. J. Biochem. 144, 217, 1984.

Pressey, R. Changes in polygalacturonase isoenzymes and converter in tomatoes during ripening. Hort Science 21, 1183, 1986.

Pressey, R. Reevaluation of the changes in polygalacturonases in tomatoes during ripening. Plants 174, 39, 1988.

Sawamura, M., Knegt, E. and Bruinsma, J. Levels of endogenous ethylene, carbon dioxide and soluble pectin and activities of pectin methylesterase and polygalacturonase in ripening of tomato fruits. Plant Cell Physiol. 19, 1061, 1978.

Seymour, G. B., Harding, S. E., Taylor, A. J., Hobson, G. E. and Tucker, G. A. Polyuronide solubilization during ripening of normal and mutant tomato fruit. Phytochemistry 26, 1871, 1987.

Sheehy, R. E., Pearson, J., Brady, C. J. and Hiatt, W. R. Molecular characterization of tomato fruit polygalacturonase. Molecular and General Genetics 208, 30, 1987.

Sheehy, R., Kramer, M. and Hiatt, W. R. Reduction of polygalacturonase activity in tomato fruit by antisense RNA. Proc. Natl. Acad. Sci. USA 85, 8805, 1988.

Smith, C. J., Watson, C. F., Ray, J., Bird, R. C., Morris, P. C., Schuch, W. and Grierson, D. Antisense RNA inhibition of polygalacturonase gene expression in transgenic tomatoes. Nature 334, 724, 1988.

Tucker, G. A., Robertson, N. G. and Grierson, D. Changes in polygalacturonase isoenzymes during the ripening of normal and mutant tomato fruit. Eur. J. Biochem. 112, 119, 1980.

Tucker, G. A., Robertson, N. G. and Grierson, D. The conversion of tomato-fruit polygalacturonase isoenzyme 2 into isoenzyme 1 in vitro. Eur. J. Biochem. 115, 87, 1981.

Tucker, G. A. and Grierson, D. Synthesis of polygalacturonase during tomato fruit ripening. Planta 155, 64, 1982.

We claim:

1. An isolated DNA sequence which encodes tomato enzyme endopolygalacturonase PG1 β-subunit or a polypeptide or peptide fragment thereof with PG1 β-subunit activity, in which the DNA sequence encodes a polypeptide or peptide which consists of or includes an amino acid sequence selected from the group consisting of:

E-K-H-S-G,

E-K-H-S-G-D-I-H, and

N-Y-G-Q-X-F-N-E-G.

2. A DNA sequence as claimed in claim 1 in which the DNA sequence encodes a polypeptide or peptide which consists of or includes the following amino acid sequence:

E-K-H-S-G.

3. A DNA sequence as claimed in claim 1 in which the DNA sequence encodes a polypeptide or peptide which consists of or includes the following amino acid sequence:

E-K-H-S-G-D-I-H.

4. A DNA sequence as claimed in claim 1 in which the DNA sequence encodes a polypeptide or peptide which consists of or includes the following amino acid sequence:

N-Y-G-Q-X-F-N-E-G.

5. An isolated DNA sequence which encodes tomato enzyme as endopolygalacturonase PG1 β-subunit, in which the DNA sequence encodes a polypeptide the N-terminal amino acid sequence of which is as follows:

E-K-H-S-G-D-I-H, and in which the polypeptide includes the following amino acid sequence:

N-Y-G-Q-X-F-N-E-G.

6. A DNA sequence as claimed in claim 1 or 5, the DNA sequence being 5' or 3' flanked by at least one heterologous DNA sequence.

7. A DNA sequence as claimed in claim 6 in which the heterologous DNA sequence is a constitutive promoter.

8. A DNA sequence as claimed in claim 7 in which the constitutive promoter is CaMV 35S.

9. A DNA sequence as claimed in claim 7 in which the heterologous DNA sequence is an inducible promoter.

10. A DNA sequence as claimed in claim 9 in which the inducible promoter is the alcohol dehydrogenase promoter.

11. A DNA construct comprising a DNA sequence as claimed in claim 1 or 5, the DNA sequence being joined in the opposite orientation for expression 5' to the 3' terminus to a transcriptional initiation region functional in tomatoes.

12. A genetically engineered tomato plant containing the DNA construct as claimed in claim 11.

13. Tomato enzyme endopolygalacturonase PG1 β-subunit protein in a substantially pure form.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Glu Lys His Ser Gly
   1               5

( 2 ) INFORMATION FOR SEQ ID NO:2:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Glu Lys His Ser Gly Asp Ile His
   1               5

( 2 ) INFORMATION FOR SEQ ID NO:3:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Glu Lys His Ser Gly Asp Ile His Gly Ala Thr Tyr Ser Asp Lys
   1               5                   10                  15

( 2 ) INFORMATION FOR SEQ ID NO:4:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Asp Ala Asn Asp Ile Glu Ala Asn Thr Tyr Asn Tyr Gly Gln Xaa Phe
   1               5                   10                  15

Asn Glu Gly ( 2 ) INFORMATION FOR SEQ ID NO:5:

( i ) SEQUENCE CHARACTERISTICS:
      ( A ) LENGTH: 11 amino acids
      ( B ) TYPE: amino acid
      ( C ) STRANDEDNESS: single ( D ) TOPOLOGY: linear ( i i ) MOLECULE TYPE: peptide ( x i ) SEQUENCE DESCRIPTION: SEQ ID NO:5:

```
Ala Leu Asn Ala Glu Asn Gln Val Arg Ile Lys
1               5                   10
```

( 2 ) INFORMATION FOR SEQ ID NO:6:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:6:

```
Glu Lys His Ser Gly Asp Ile His Gly Ala Thr Tyr Ser Asp Lys
1               5                   10                  15
```